United States Patent [19]

Petersen et al.

[11] Patent Number: 4,728,496

[45] Date of Patent: Mar. 1, 1988

[54] APPARATUS AND METHOD FOR CONTROL AND STERILIZATION OF FLUID FLOW

[75] Inventors: Preben A. Petersen, Bjarred; Jan P. Sternby, Lund, both of Sweden

[73] Assignee: Gambro AB, Sweden

[21] Appl. No.: 868,353

[22] Filed: May 29, 1986

[30] Foreign Application Priority Data

Jun. 4, 1985 [SE] Sweden .............................. 8502758

[51] Int. Cl.$^4$ ............................................. F16K 49/00
[52] U.S. Cl. ........................................ 422/1; 137/340; 210/321.2; 210/321.72; 210/321.69
[58] Field of Search ........................... 422/1; 137/340; 210/321.2, 321.3

[56] References Cited

U.S. PATENT DOCUMENTS 3,738,382 6/1973 Cappelen et al. ..................... 137/1
4,122,010 10/1978 Riede et al. ............................ 210/90

*Primary Examiner*—Barry S. Richman
*Assistant Examiner*—William R. Johnson

*Attorney, Agent, or Firm*—Lerner, David, Littenberg, Krumholz & Mentlik

[57] ABSTRACT

Apparatus and methods for controlling and sterilizing the flow of fluids through a medical treatment device such as a dialyzer including a fluid flow inlet for feeding the fluid to the medical treatment device, a heater for controlling the supply of heat to the fluid in the fluid flow inlet, a fluid flow outlet for withdrawing contaminated fluid from the dialyzer, a recirculation duct for recirculating at least a portion of the heated fluid from a point in the fluid flow inlet to an upstream point in the fluid flow inlet in which the heated fluid can again pass through the heater, and valves for selectively directing at least a portion of the fluid to the recirculation duct for sterilization purposes. The method further includes flowing the fluid through a fluid flow inlet, supplying heat to the fluid in the fluid flow inlet, feeding the heated fluid to the dialyzer, withdrawing contaminated fluid from the dialyzer, and intermittently recirculating at least a portion of the heated fluid from a point upstream of the dialyzer to a point in the fluid flow inlet whereby the recirculated heated fluid can again pass through the heater so that the fluid flow inlet can be sterilized thereby.

9 Claims, 1 Drawing Figure

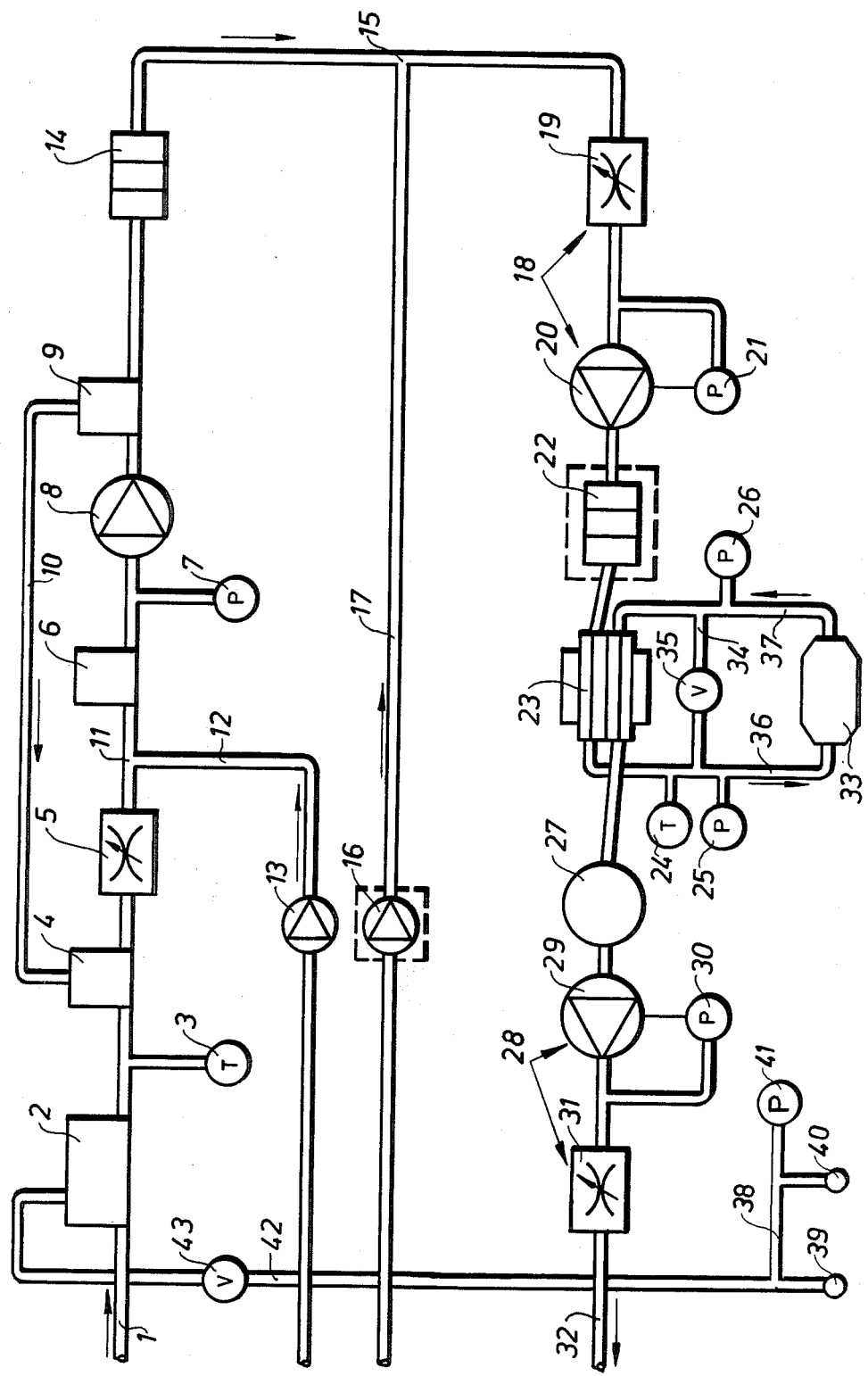

APPARATUS AND METHOD FOR CONTROL AND STERILIZATION OF FLUID FLOW

FIELD OF THE INVENTION

The present invention relates to apparatus for the control of medical treatments, such as dialysis and the like, and more particularly to apparatus for such medical treatment using a tempered or heated fluid and including means for controlling the temperature and the flow of this fluid therein. More particularly, the present invention relates to such apparatus including means for connecting the system to a treating device, such as a dialyzer, for disinfection and/or sterilization by means of a fluid which is heated to a temperature higher than that of normal treatment.

The present invention also relates to a method for controlling and sterilizing such fluid flow through a medical treatment device such as a dialyzer or the like. Most particularly, the present invention relates to such methods and apparatus for controlling hemodialysis, i.e. for purifying blood of patients having diminished or nil renal function. The present invention also relates to such systems for controlling other such medical treatments such as peritoneal dialysis, hemofiltration, plasmafers, and other such systems in which means for tempering or heating the treatment fluid is included therein.

BACKGROUND OF THE INVENTION

The present invention particularly relates to an improvement in the system presenting being marketed by the Gambro Group, to which the assignee of the present application belongs, under the description "Gambro AK-10".

Various details of this system form the subject of, for example, U.S. Pat. Nos. 4,122,010; 4,158,034; 4,293,409; 4,194,974; and 4,191,359; and the descriptions of this system set forth therein are incorporated herein by reference thereto, as are the further improvements thereon disclosed in European patent application No. 84.112914, and the invention according to British Pat. No. 2,003,274, and European patent application No. EP 0 106 940, which are also incorporated herein by reference thereto. Reference is also made to EP No. 0 022 922, which describes in more detail the preparation of dialysis fluid from two concentrates, a preparation which is only touched upon in the following description of the present invention.

Finally, reference is made to U.S. Pat. No. 3,738,382, which describes a different system for the preparation of dialysis fluid in which sterilization is achieved by means of a heating element which is normally included in the system, while at the same time heated sterilizing agent is recirculated through the system in its entirety. Such a system is thus subject to the disadvantage, among other things, that the sterilizing fluid is recirculated through both the less contaminated as well as the more contaminated portions of the system. As a result, impurities may be passed from the more contaminated portions to the less contaminated portions of the system. Furthermore, known systems are designed to operate at pressures above atmospheric pressure, which is applicable only to very unique procedures for the preparation of dialysis fluid, and as a result its applicability is rather limited.

SUMMARY OF THE INVENTION

In accordance with the present invention, applicants have discovered an apparatus and method for controlling and sterilizing the flow of a fluid through a medical treatment device such as a dialyzer or the like. In accordance with the apparatus of the present invention, there is disclosed a fluid flow inlet path for feeding the fluid to the medical treatment device, temperature control means including heating means for controlling the supply of heat to said fluid at a predetermined heating location in the fluid flow inlet path, a fluid flow outlet path for withdrawing contaminated fluid from the medical treatment device, recirculation means for recirculation of at least a portion of the heated fluid from a point in the fluid flow inlet path which is upstream of the medical treatment device to a point further upstream in the fluid flow inlet path whereby the heated fluid again passes through the predetermined heating location, and selective actuation means for selective actuation of the recirculation means when it is desired to sterilize the apparatus, whereby the apparatus can be sterilized by increasing the supply of heat to the fluid from the temperature control means so as to raise the temperature of the fluid to a temperature above the predetermined treatment temperature and selectively actuating the selective actuation means whereby at least a portion of the fluid is recirculated through the recirculation means while at the same time recirculation does not take place from a point downstream of the medical treatment device where the contaminated fluid normally flows.

In accordance with a preferred embodiment of the apparatus of the present invention, the medical treatment device comprises a dialyzer, and preferably ultrafiltration is carried out across a membrane within the dialyzer so as to produce a dialysate as the contaminated fluid therein.

In accordance with another embodiment of the apparatus of the present invention, the temperature control means is adapted to raise the temperature of the fluid to about 90° C. so that during sterilization the temperature of the portion of the fluid which is recirculated is also heated to about 90° C., and at the same time the temperature of the fluid downstream of the recirculation means is permitted to drop to temperatures of about 80° C.

In accordance with the method of the present invention, the method includes flowing the fluid through a fluid flow inlet path, controllably supplying heat to the fluid at a predetermined heating location in the fluid flow inlet path, feeding the heated fluid to the medical treatment device, withdrawing contaminated fluid from the medical treatment device, and intermittently recirculating at least a portion of the heated fluid from a point upstream of the medical treatment device to a point in the fluid flow inlet path so that at least a portion of the heated fluid again passes through the predetermined heating location whereby the fluid flow inlet path may be sterilized by increasing the supply of heat to the fluid at the predetermined heating location so as to raise the temperature of the fluid to a temperature above the predetermined heating temperature while the intermittent recirculation does not take place from a point downstream of the medical treatment device where the contaminated fluid normally flows.

In accordance with another embodiment of the method of the present invention, heat is controllably supplied to the fluid at the predetermined heating location which is sufficient to raise the temperature of the fluid to an elevated temperature of about 90° C. so that during the sterilization the temperature of at least the portion of the fluid which is recirculated is also heated to about 90° C., while the temperature of the fluid downstream of the recirculation means is permitted to drop to a temperature of about 80° C.

In accordance with another embodiment of the apparatus of the present invention, the apparatus includes a system in which a part of the fluid heated to a temperature which is higher than the normal treatment temperature is recirculated in the system. The advantages gained by use of this design are that the very same heating devices which are normally included in the system now suffice, without overdimensioning, both to compensate for heat losses in the recirculating system as well as for heating a small amount of new fluid which is continuously supplied thereto. At the same time, an amount of fluid which is equal to the amount of that newly supplied fluid is allowed to flow through the more contaminated portions of the system directly to an outlet.

In accordance with a preferred embodiment of the present invention, the recirculation is arranged so as to take place through a special return line which runs from a downstream point in the system to a further upstream point, preferably at the start of the system. This special return line is appropriately adapted so that recirculation takes place from a bypass arrangement, that is to say it takes place within that portion of the system which normally contains pure treatment fluid which has not been affected or contaminated by the treatment device itself. It may thus also be insured that no recirculation takes place in that portion of the system through which treatment fluid normally flows which has already been acted on by the treatment device, and which may thus have been contaminated thereby.

In that embodiment where the present invention is merely intended to procure disinfection, the normal heating device used in this system may be adapted so as to raise the temperature in a fluid heating vessel to approximately 90° C., while the temperature in the system downstream of the recirculation point may be allowed to gradually drop, e.g. down to a temperature of the order of magnitude of about 80° C.

In accordance with another embodiment of the method of the present invention, disinfection and/or sterilization are adapted to take place substantially at normal atmospheric pressures. However, if it is desired to insure effective sterilization, it may become necessary to either increase the pressure and the temperature, or to supplement same by chemical means.

In practice it has proven to be helpful to conduct disinfection and/or sterilization with maximum flow in the recirculation circuit, while the flow in the rest of the system is maintained at a fraction thereof, e.g. on the order of magnitude of about one-fifth thereof.

Any constrictions which are to be included in the recirculation circuit are preferably incorporated therein so that they can be opened or wholly or partially bridged over during disinfection and/or sterilization so as to minimize the flow resistance therein.

BRIEF DESCRIPTION OF THE DRAWINGS

The present invention is described in more detail in the following Detailed Description, which refers to the drawing, which shows an example of the most important components of a system in accordance with the present invention.

DETAILED DESCRIPTION

Referring to the drawing, in the example of this invention shown therein water is fed through inlet 1 to a heating device 2, where it is heated. The temperature of the fluid therein is then measured in a temperature measuring device 3 before the water-containing fluid is conducted through a return vessel 4 to a constriction 5, and then through a bubble expansion tank 6, a pressure gauge 7, and a pump 8, to a vent tank 9. From vent tank 9 a return duct 10 leads back to return vessel 4 in order to accomplish recycle of any air or other gases which are separated along with a small portion of the fluid. Such recycle could also possibly be made instead to the heating vessel 2, but doing so would then require that said vessel 2 be made from a more resistant material, since dialysis concentrate is being supplied to point 11 through duct 12, with the help of pump 13. This portion of this system substantially corresponds to the system described, for example, in U.S. Pat. Nos. 4,158,034 and 4,293,409. Also, the function of expansion vessel 6 is described in detail in European patent application No. 84.112914.1. From vent tank 9 the fluid is then passed through conductivity measuring cell 14 to another mixing point 15, where further concentrate is supplied, in this case possibly with the assistance of a pump 16 and a duct 17. This is done where it is intended to work with a so-called two-component-based dialysis concentrate, e.g. of the type described in EP No. 0 022 922.

From mixing point 15 the dialysis fluid is then passed through a first constant flow arrangement 18, which consists of constriction 19, pump 20 and pressure gauge 21. Before (upstream of) the constriction device 19 the pressure is substantially at atmospheric pressure, as this duct is connected to the vent tank 9 without any major resistance. Should it be found in practice that there is a variation in pressure due to the pump 16, the conductivity meter 14 and the mixing point 15 can be moved to a position prior to (upstream of) the vent tank 9.

The pressure measured by pressure gauge 21 can then be used to control the pump 20, so that a desired constant flow can thus be obtained. Downstream of the pump 20 the fluid passes through a conductivity meter 22 and an ultrafiltration monitor 23, and then through a temperature measuring instrument 24 and a pressure gauge 25, to dialyzer 33. From the dialyzer the fluid flow is then conducted through a pressure gauge 26, the ultrafiltration monitor 23, and a blood detector 27, to a further constant flow arrangement 28, in this case consisting of a pump 29, a pressure gauge 30, and a constriction device 31. Finally, the dialysate is passed to an outlet 32. It is preferred that the constant flow arrangement 28 be identical to the constant flow arrangement 18. In the constriction 31, however, the pressure drop which is obtained is from a pressure which is above atmospheric to the pressure prevailing at the outlet, which should be kept constant and, for example, may be equal to atmospheric pressure.

The design and function of the ultrafiltration monitor 23 are described in greater detail in the above-mentioned publications, namely British Pat. No. 2,003,274 and EP No. 0 106 940.

Reference numeral 33 designates the dialyzer, which can be connected to the system in accordance with the invention. The patient is thus connected to the blood side of the dialyzer 33. This latter connection, however, is not shown in the drawing.

The dialyzer 33 can be bridged over in two ways. This may be accomplished either by means of a by-pass duct 34, along with valve 35 which can be opened, for example, if the temperature or the conductivity vary outside of certain predetermined upper and lower limit values. At the same time, the flow to the dialyzer 33 can be terminated by means of a valve which is not shown in the drawing, however.

Alternatively, this bridging may be accomplished by coupling dialyzer connections 36 and 37 to a by-pass duct 38 via couplings 39 and 40. This bridging arrangement appropriately designed primarily according to U.S. Pat. No. 4,122,010 with a pressure monitoring device 41, which determines whether a suction pressure exists in duct 38. In the present case, however, this device detects instead a pressure above atmospheric pressure. If this is the case, and only if this is the case, sterilization may then take place.

In the example shown in the drawing a return duct 42, containing a valve 43, runs back from bridging arrangement 38 to the heating vessel 2. A portion of the fluid flow can thus be recirculated through this duct 42 when the system is to be disinfected or sterilized. The remaining portion of the flow passes instead through duct 36, which is connected to coupling 39 via duct 38 and coupling 40 to duct 37, and from there through the ultrafiltration monitor 23 to the outlet 32. A small amount, however, is conducted directly from duct 36 through duct 34, containing valve 35, directly to duct 37 for disinfection and/or sterilization of this bridging arrangement.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A method for controlling the flow of a fluid through a medical treatment device which subjects said fluid to contamination and in which said fluid is normally maintained at a predetermined treatment temperature, said method comprising flowing said fluid through a fluid flow inlet path, controllably supplying heat to said fluid at a predetermined heating location in said fluid flow inlet path, feeding said heated fluid to said medical treatment device, withdrawing said contaminated fluid from said medical treatment device, and intermittently recirculating at least a portion of said heated fluid from a point upstream of said medical treatment device to a point in said fluid flow inlet path upstream of said predetermined heating location so that said at least a portion of said heated fluid again passes through said predetermined heating location whereby said fluid flow inlet path may be disinfected or sterilized by recirculating said fluid through said predetermined heating location so as to raise the temperature of said fluid to a temperature above said predetermined heating temperature while said intermittent recirculation does not take place from a point downstream of said medical treatment device where said contaminated fluid normally flows.

2. The method of claim 1 wherein said controllably supplying heat to said fluid at said predetermined heating location is sufficient to raise the temperature of said fluid to an elevated temperature of about 90° C. whereby during said sterilizing said temperature of said at least a portion of said fluid is also heated to a temperature of about 90° C. while the temperature of said fluid downstream of said predetermined heating location drops to a temperature of about 80° C.

3. The method of claim 1 including maintaining the pressure in said predetermined fluid flow path substantially constant.

4. The method of claim 3 wherein said substantially constant pressure comprises atmospheric pressure.

5. The method of claim 1 wherein said intermittently recirculated portion of heated fluid comprises the major portion of said heated fluid, whereby only a minor portion of said heated fluid is withdrawn from said medical treatment device.

6. The method of claim 5 wherein said minor portion of said heated fluid comprises about one-fifth of the total volume of said heated fluid.

7. Apparatus for controlling the flow of a fluid through a medical treatment device which subjects said fluid to contamination and in which said fluid is normally maintained at a predetermined treatment temperature, said apparatus comprising a fluid flow inlet path for feeding said fluid to said medical treatment device, temperature control means including heating means for controlling the supply of heat to said fluid at a predetermined heating location in said fluid flow inlet path, a fluid flow outlet path for withdrawing said contaminated fluid from said medical treatment device, recirculation means for recirculation of at least a portion of said heated fluid from a point in said fluid flow inlet path upstream of said medical treatment device to a point further upstream in said fluid flow inlet path which is upstream of said predetermined heating location whereby said heated fluid again passes through said predetermined heating location, and selective actuation means for selective actuation of said recirculation means when it is desired to sterilize said apparatus, whereby said apparatus can be disinfected or sterilized by recirculating said fluid through said temperature control means so as to raise the temperature of said fluid to a temperature above said predetermined treatment temperature and selectively actuating said selective actuation means whereby said at least a portion of said fluid is recirculated through said recirculation means while at the same time said recirculation does not take place from a point downstream of said medical treatment device where said contaminated fluid normally flows.

8. The apparatus of claim 7 wherein said temperature control means is adapted to raise the temperature of said fluid to an elevated temperature of about 90° C., whereby during sterilization the temperature of said at least a portion of said fluid recirculated in said recirculation means is also heated to a temperature of about 90° C. while the temperature of said fluid downstream of said temperature control means drops to a temperature of about 80° C.

9. The apparatus of claim 7 wherein said medical treatment device comprises a dialyzer whereby said contamination of said fluid comprises the production of a dialysate therein.

* * * * *